United States Patent
Elbeih et al.

(10) Patent No.: US 9,227,981 B2
(45) Date of Patent: Jan. 5, 2016

(54) METHOD OF PREPARATION OF EPSILON-2,4,6,8,10,12-HEXANITRO-2,4,6,8,10,12-HEXAAZAISOWURTZITANE WITH REDUCED IMPACT SENSITIVITY

(71) Applicant: UNIVERSITY OF PARDUBICE, Pardubice (CZ)

(72) Inventors: Ahmed Ikhlas Mohamed Elbeih, Cario (EG); Adela Husarova, Ostrava (CZ); Svatopluk Zeman, Pardubice (CZ)

(73) Assignee: UNIVERSITY OF PARDUBICE, Pardubice (CZ)

( * ) Notice: Subject to any disclaimer, the term of this patent is extended or adjusted under 35 U.S.C. 154(b) by 82 days.

(21) Appl. No.: 14/347,511

(22) PCT Filed: Oct. 1, 2012

(86) PCT No.: PCT/CZ2012/000098
§ 371 (c)(1),
(2) Date: Mar. 26, 2014

(87) PCT Pub. No.: WO2013/044891
PCT Pub. Date: Apr. 4, 2013

(65) Prior Publication Data
US 2014/0235853 A1     Aug. 21, 2014

(30) Foreign Application Priority Data
Sep. 29, 2011  (CZ) .................................... 2011-608

(51) Int. Cl.
*C07D 487/22*    (2006.01)
(52) U.S. Cl.
CPC ................................ *C07D 487/22* (2013.01)

(58) Field of Classification Search
CPC ...................................................... C07D 487/22
USPC ........................................................... 540/554
See application file for complete search history.

(56) References Cited

FOREIGN PATENT DOCUMENTS

| CN | 200910090462.6 | 8/2009 |
| CN | 101 624 394 | 1/2010 |
| KR | 10-0224043 | 7/1999 |
| WO | 2011/039459 | 4/2011 |

OTHER PUBLICATIONS

Hu Li-Shuang, Study on the application of the supercritical solution technology in preparation of Ultra-fine and sphere CL-20, Journal of Safety Science and Technology, Jun. 2010, vol. 6, No. 3.
Anthony J. Bellamy, A Simple Method for the Purification of Crude Hexanitrohexaazaisowurtzitane (HNIW or CL20), Propellants, Explosives, Pyrotechnics vol. 28, No. 3, 2003, Weinheim.
Sivabalan et al: "Study on ultrasound assisted precipitation of CL-20 and its effect on morphology and sensitivity", Journal of Hazardous Materials, Elsevier, Amsterdam, NL,vol. 139. No. 2, Dec. 2006, pp. 199-203.
International Search Report for PCT/CZ2012/000098, Dec. 5, 2012.

*Primary Examiner* — Brenda Coleman
(74) *Attorney, Agent, or Firm* — Notaro, Michalos & Zaccaria P.C.

(57) ABSTRACT

The present invention relates to a method of preparation of ε-2,4,6,8,10,12-hexanitro-2,4,6,8,10,12-hexaazaisowurtzitane with reduced impact sensitivity by precipitation of a solution of 2,4,6,8,10,12-hexanitro-2,4,6,8,10,12-hexaazaisowurtzitane in a solvent by an antisolvent, wherein phosphorus(V) oxide is added as a recrystallization promoter to the solution of 2,4,6,8,10,12-hexanitro-2,4,6,8,10,12-hexaazaisowurtzitane in the solvent, the obtained mixture is stirred and filtered, and the filtrate is subsequently precipitated by the addition of the antisolvent.

10 Claims, No Drawings

METHOD OF PREPARATION OF EPSILON-2,4,6,8,10,12-HEXANITRO-2,4,6,8,10,12-HEXAAZAISOWURTZITANE WITH REDUCED IMPACT SENSITIVITY

RELATED APPLICATIONS

This is a national stage application based on international patent application PCT/CZ2012/000098, filed Oct. 1, 2012. Priority is also claimed to Czech Republic application number PV 2011-608, filed Sep. 29, 2011.

FIELD OF ART

The invention concerns a method of preparation of the polynitro compound ϵ-2,4,6,8,10,12-hexanitro-2,4,6,8,10,12-hexaazaisowurtzitane (ϵ-HNIW, ϵ-CL20) in the form of the modification with reduced impact sensitivity (RS-CL20).

BACKGROUND ART

The target polynitro compound, ϵ-2,4,6,8,10,12-hexanitro-2,4,6,8,10,12-hexaazaisowurtzitane (hereinafter only ϵ-CL20) belongs to the group of polycyclic nitramines and finds applications predominantly in military high explosive mixtures and propellants (Song Zhenwei; Li Xiaojiang: Recent research progress and application prospect of high energy density compound HNIW, Huaxue Tuijinji Yu Gaofenzi Cailiao (2011), 9(1), 40-45; U. R. Nair, R. Sivabalan, G. M. Gore, M. Geetha, S. N. Asthana, H. Singh: Hexanitrohexaazaisowurtzitane (CL-20) and CL-20-based formulations, Combustion, Explosion, and Shock Waves, (2005) 41(2) 121-132). This high explosive belongs among those with the highest performance, but its wider use is hindered by relatively high manufacturing costs and particularly by its unsatisfactory sensitivity—there still prevails the view that the sensitivity of CL20 is approximately at the level of that of pentaerythritol tetranitrate (PETN), i.e. max. 4 J in the impact sensitivity (U. R. Nair, R. Sivabalan, G. M. Gore, M. Geetha, S. N. Asthana, H. Singh: Hexanitrohexaazaisowurtzitane (CL-20) and CL-20-based formulations, Combustion, Explosion, and Shock Waves, (2005) 41(2) 121-132). The sensitivity, particularly the impact sensitivity, of this type of compounds is affected by the purity of the nitramine as well as by the size, break-down rate and shape of its crystals. A perfect removal of side products from the crystals of CL20 is not easy and, therefore, the standard NATO STANAG-4566 allows their maximum content in the final product to be 3% w/w. The break-down rate of the crystals, i.e. their porosity and cracks, is connected with the recrystallization method and the solvents chosen for the recrystallization; as far as the shape of the crystals is concerned, desirable are spherical particles or, more precisely, crystals with rounded edges. The literature comprises a large number of articles about the recrystallization of CL20 (e.g., N. Degirmenbasi, Z. Penalta-Inga, U. Olgun, H. Gocmez, D. M. Karyon: Recrystallization of CL20 and HNFX from solution for rigorous control of the polymorph type: Part II, experimental studies, Journal of Energetic Materials (2006) 24, 103-139).

The recrystallization of CL20, which is focused on the preparation of its technologically most attractive ϵ-modification, mostly involves the application of a "solvent-antisolvent" system (the product is precipitated from its solution by the addition of another solvent in which it is poorly soluble or completely insoluble). The solvents used in this method often include ethyl acetate or its mixture with toluene, but there are other solvents patented, e.g., methyl acetate, isopropyl acetate, butyl acetate, tetrahydrofurane, methyl ethyl ketone, cyclohexanone, acetonitrile and acetone. When α-CL (which, being a hemihydrate, contains crystal water) is the starting modification used for the recrystallization, water must be removed from the solution of α-CL either by addition of a drying agent, such as magnesium or sodium sulfate, potassium carbonate or silica gel, or by azeotropic distillation with ethyl acetate, or ethyl acetate and toluene. The thus dried and optionally subsequently filtered CL20 solution is concentrated for recrystallization (when the ethyl acetate plus toluene mixture is used) or precipitated in a predefined way by addition of hexane, heptane, cyclohexane, octane, petroleum ether, dichloromethane, trichloromethane, benzyl acetate, benzyl formate, toluene, xylene or even benzene (WO 99/57104; U.S. Pat. Nos. 5,973,149; 5,874,574; US 2003/0130503; US 2003/636373; JP 11322752; EP 0913374). However, this method does not necessarily lead to a substantial reduction of the content of impurities in the product. The laboratory methods of preparation of highly pure CL20 include filtration with charcoal, e.g., in the amount of 20 g charcoal per 1 g CL20 (A. J. Bellamy: A simple method for the purification of crude hexanitrohexaazaisowurtzitane, Propellants, Explosive, Pyrotechnics, (2003) 28(3) 145-152) or column chromatography of benzene solution of CL20 (Ou Yuxiang et al.: Synthesis and crystal structure of β-hexanitrohexaazaisowurtzitane, Science in China, Series B, (1999) 42(2) 218-224).

All the above described recrystallization methods destined for the preparation of ϵ-CL20 yield a product having the impact sensitivity of about 4 J, which restricts its application as an active component particularly in special military ammunition.

Only four publications deal with the preparation of the very attractive ϵ-CL20 with spherical crystals (i.e. crystals with rounded edges exhibiting the reduced impact sensitivity, RS-CL20):

a) in the application of the "solvent-antisolvent" system, the solution of CL20 in ethyl acetate was precipitated by addition of heptane fraction with a simultaneous ultrasound treatment (R. Sivabalan, G. M. Gore, U. R. Nair, A. Saikia, S. Venugopalan, B. R. Gaandhe: Study on ultrasound-assisted precipitation of CL20 and its effect on morphology and sensitivity, Journal of Hazardous Materials (2007) A139, 199-203); this sonication shortened the precipitation time and yielded RS-CL20 crystals exhibiting impact sensitivities of 5.9 J to 10.8 J. However, the description of the procedure does not mention how the procedure affected the product purity.

b) according to the Chinese patent document CN 101624394 (2010), a recrystallization promoter is added into the solution before precipitation; the promoter may include organic compounds of the amino acid group, such as glycine, alanine etc., and esters of these amino acids, polyols, such as poly(vinyl alcohol), glycerol, pentaerythritol and others, organic acids, such as butanecarboxylic, maleic, malonic, adipic acid etc., and esters of these acids. The RS-CL20 obtained in this way has the purity above 98% and the impact sensitivity of 5.6 to 10.2 J. A similar procedure is protected by a Korean patent KR 224043 (1999) describing the use of pyridine as the promoter and yielding RS-CL20 with the impact sensitivity of 8.1 J.

c) Chinese authors also used a precipitation recrystallization from supercritical solution of CL20 in liquid carbon dioxide (gas-antisolvent; Hu Li-shuang, Hu Shuang-qi: Study on the application of the supercritical solution technology in preparation of Ultra-fine and sphere CL-20; Zhongguo Anquan Shengchan Kexue Jishu (2010), 6(3), 80-83). This method is demanding with respect to the necessary technological equipment (high pressures).

The aim of the present invention is, while taking into account the above-mentioned findings about the so far known procedures of preparation of RS-CL20, to provide a new procedure, which—without high demands for the equipment and materials—would yield the required spherical crystals of the product, while at the same time substantially decreasing the amount of impurities in the final product and ensuring reproducibility in achieving the reduced impact sensitivity.

DISCLOSURE OF THE INVENTION

The object of the present invention is a method of preparation of the polynitroamine ε-2,4,6,8,10,12-hexanitro-2,4,6,8,10,12-hexaazaisowurtzitane (ε-HNIW, ε-CL20) with reduced impact sensitivity (RS-CL20) by precipitation of a solution of 2,4,6,8,10,12-hexanitro-2,4,6,8,10,12-hexaazaisowurtzitane (CL20) in a solvent by an antisolvent, wherein phosphorus(V) oxide is added as the recrystallization promoter to the solution of 2,4,6,8,10,12-hexanitro-2,4,6,8,10,12-hexaazaisowurtzitane (CL20) in the solvent, before or after an optional removal of water from the solution; the obtained mixture is stirred and filtered, and the filtrate is precipitated by the addition of the antisolvent. The required modification RS-CL20, i.e., ε-2,4,6,8,10,12-hexanitro-2,4,6,8,10,12-hexaazaisowurtzitane with crystals having rounded edges and eliminated defects, which has reduced impact sensitivity, precipitates from the solution. Finally, the product can be isolated by known procedures, e.g., filtration and drying of the solid phase.

The preparation of CL20 can be performed by known procedures.

The removal of water from the solution is suitable particularly when α-CL20 hemihydrate is used as the starting material.

In a preferred embodiment, the solvent for the starting CL20 solution is ethyl acetate.

Preferably, the recrystallization promoter phosphorus(V) oxide is used in the amount of 1 to 15% w/w, more preferably 1 to 5% w/w, most preferably 3.57% w/w, relative to the weight of CL20.

Together with phosphorus(V) oxide, the known promoters can be used, e.g., glycerol.

When crude CL20 is used for the recrystallization, then after the addition of phosphorus(V) oxide the formed phosphoric acid and polyphosphoric acid bind the side products from the synthesis of the CL20, including 4,6,8,10,12-pentanitro-2-monooxo-4,6,8,10,12-pentaazaisowurtzitane, 4,6,8,10-tetranitro-2,12-dioxotetraazaisowurtzitane, 2-acetyl-4,6,8,10,12-pentanitro-4,6,8,10,12-hexaaazaisowurtzitane, 2,6,8,12-tetraacetyl-4,10-dinitrohexaazaisowurtzitane and 4,10-dinitro-2,6,8,12-tetraoxadiazaisowurtzitane. These and other side products together with the polyphosphoric acid spontaneously separate from the solution of CL20 in the form of brownish sticky mass. The recrystallization without the addition of the promoter (batch 26 in Table 1) gave ε-CL20 of "ordinary" impact sensitivity.

The stirring of the mixture of CL20 solution with the recrystallization promoter is preferably performed for a time period within the range of 15 to 60 min.

The stirring of the mixture of the CL20 solution with the recrystallization promoter is preferably performed at a temperature within the range of 10 to 40° C.

The antisolvent is preferably selected from the group comprising paraffinic hydrocarbons, polychlorinated aliphatic hydrocarbons and aromatic hydrocarbons and their derivatives, more preferably from the group comprising hexane, heptane, octane, cyclohexane, petroleum ether, dichloromethane, chloroform, benzyl acetate, benzyl formate, toluene, benzene and xylene.

In a preferred embodiment, ultrasound is applied during the precipitation step and/or the mixture is stirred.

In one preferred embodiment, n-heptane is used as the antisolvent; the filtrate is transferred into n-heptane, whereas the precipitation is performed with stirring, preferably with application of ultrasound acting upon the antisolvent during the precipitation.

In another preferred embodiment, xylene or chloroform is used as the antisolvent, whereas the antisolvent is added to the filtrate which is stirred with a mechanical stirrer.

In a particularly preferred embodiment, the preparation of RS-CL20 is performed by removing water from CL20 solution in ethyl acetate by means of vacuum azeotropic distillation, subsequently adding to the dehydrated solution 3.57% w/w recrystallization promoter phosphorus(V) oxide, relative to the weight of CL20, maintaining this mixture for 15 min at the temperature of 20° C., filtering the resulting mixture and precipitating the final product by means of addition of n-heptane or xylene. This procedure gave RS-CL20 with the lowest impact sensitivity and the highest purity.

EXAMPLES OF CARRYING OUT THE INVENTION

Example 1

Preparation of RS-CL20

A charge of 31.5 mass parts of ethyl acetate is treated with 7 mass parts of crude α-CL20. Stirring at the stirrer frequency of ca 400 rpm results in dissolution of the CL20, which takes 10 to 15 min, and the obtained solution is filtered in order to remove mechanical impurities, if any. The filtrate can optionally be concentrated. Subsequently, it is dehydrated (removal of water) by vacuum azeotropic distillation to reduce its original volume to approximately seven tenths, whereupon the recrystallization promoter, phosphorus(V) oxide, is added to it in the amount specified in Table 1. Then the mixture is stirred at the given temperature for a given period of time (see Table 1). After the stirring period, the solution is filtered, and the filtrate is added dropwise into 51.3 mass parts of n-heptane, acting as the antisolvent, which is placed in an ultrasound bath for better stirring and formation of smaller crystals. The formed suspension is filtered and the thus prepared RS-CL20 is dried in a vacuum drying oven for 10 hours.

The products of individual batches of RS-ε-CL20 are examined by means of the Kast's falling hammer to determine the impact sensitivity (for the 50% probability of initiation according to the public notice of ČBÚ (Czech Mining Authority) No. 246/1996), and their purity is determined by means of HPLC using the solvent system of acetonitrile-water (60:40) and an Agilen column. Using the vacuum stability test STABIL, some of the samples are exposed to the temperature of 120° C. for a time period of 48 hours in order to determine the amount of gaseous decomposition products (ml of gas per 1 g of the sample). The results of these tests are shown in Table 1. In this table, the data given for batch 26 represent ε-CL20 of ordinary quality (standard sample), which was prepared by recrystallization (precipitation) without promoter (i.e. without phosphorus(V) oxide); this procedure was a reproduction of that described in the above-recited Journal of Hazardous Materials (2007) A139, 199-203, but it did not give the results declared by the authors of this article. For comparison, Table 1 also presents the data for the starting α-CL20.

TABLE 1

Conditions of processing of crude CL20 to obtain final RS-CL20, its purity and sensitivity characteristics

| Batch | Vacuum distillation | Amount of $P_2O_5$ in % of CL20 | Stirring time (min) | Stirring temperature (°C.) | Purity of RS-CL20 (% w/w) | Impact sensitivity (J) | STABIL (ml/g) after 48 hours |
|---|---|---|---|---|---|---|---|
| 1 | no | 3.57 | 15 | 20 | 98.66 | 7.4 | |
| 2 | no | 7.14 | 15 | 20 | 99.13 | 7.8 | |
| 3 | no | 10.71 | 15 | 20 | 98.42 | 8.2 | |
| 4 | no | 14.28 | 15 | 20 | 98.11 | 7.2 | |
| 5 | yes | 3.57 | 15 | 20 | 99.80 | 10.8 | 0.131 |
| 6 | yes | 7.14 | 15 | 20 | 98.89 | 10.2 | |
| 7 | yes | 10.71 | 15 | 20 | 99.72 | 9.3 | |
| 8 | yes | 14.28 | 15 | 20 | 98.49 | 9.2 | |
| 9 | yes | 3.51 | 30 | 20 | 99.54 | 8.8 | |
| 10 | yes | 7.14 | 30 | 20 | 99.11 | 8.5 | |
| 11 | yes | 10.71 | 30 | 20 | 98.52 | 8.6 | |
| 12 | yes | 3.51 | 60 | 20 | 99.04 | 9.6 | |
| 13 | yes | 7.14 | 60 | 20 | 98.88 | 9.3 | |
| 14 | yes | 10.71 | 60 | 20 | 98.45 | 8.1 | |
| 15 | yes | 3.51 | 15 | 30 | 99.63 | 9.8 | |
| 16 | yes | 7.14 | 15 | 30 | 99.44 | 8.9 | |
| 17 | yes | 10.71 | 15 | 30 | 99.46 | 8.4 | |
| 18 | yes | 1.43 | 15 | 30 | 99.57 | 8.2 | |
| 19 | yes | 3.51 | 15 | 40 | 98.78 | 8.7 | |
| 20 | yes | 7.14 | 15 | 40 | 98.36 | 7.9 | 0.182 |
| 21 | yes | 10.71 | 15 | 40 | 98.29 | 8.1 | |
| 22 | yes | 1.43 | 15 | 40 | 97.98 | 7.6 | |
| 23 | yes | 3.51 | 15 | 10 | 98.47 | 7.4 | |
| 24 | yes | 3.51* | 15 | 20 | 99.29 | 7.1 | 0.229 |
| 25 | yes** | 3.51 | 15 | 20 | 99.58 | 9.6 | 0.146 |
| 26 | yes | 0 | 15 | 20 | 99.00 | 4.1 | 0.243 |
| α-CL20 | — | — | — | — | 97.40 | 1.9 | 0.334 |

Notes:
*)simultaneous addition of 12.8% w/w glycerol calc. on mass of α-CL20;
**)vacuum dehydration with addition of phosphorus(V) oxide in solution Example 2

Preparation of RS-CL20 by Precipitation with Xylene

A charge of 31.5 mass parts of ethyl acetate is treated by addition of 7 mass parts of crude α-CL20. The added CL20 is dissolved after 10-15 min stirring at the stirrer speed of ca 400 rpm, and the formed solution is filtered to remove mechanical impurities, if any. The filtrate is concentrated in vacuum and dehydrated by azeotropic distillation to obtain approximately seven tenths of the original volume, whereupon the recrystallization promoter, phosphorus(V) oxide, is added to it in the amount of 3.57% w/w, relative to the starting charge of α-CL20, and then the mixture is stirred at the temperature of 20° C. for a period of 15 min. After this stirring period, the solution is filtered, and the filtrate is stirred (400 rpm) and treated with 65.25 mass parts of xylene (acting as antisolvent) added dropwise. Subsequently the formed suspension is filtered and the thus prepared RS-CL20 is dried in a vacuum drying oven for a period of 10 hours. The obtained RS-CL20 has the purity of 99.24%, impact sensitivity of 9.2 J, and the result of its vacuum stability test is 0.178 ml/g/48 hours at the temperature of 120° C.

Example 3

Preparation of RS-CL20 by Precipitation with Chloroform

A charge of 31.5 mass parts of ethyl acetate is treated by addition of 7 mass parts of crude a-CL20. The added CL20 is dissolved after 10-15 min stirring at the stirrer speed of 400 rpm, and the obtained mixture is filtered to remove possible mechanical impurities. The filtrate is concentrated in vacuum and dehydrated by azeotropic distillation to obtain approximately seven tenths of its original volume, and then the recrystallization promoter, phosphorus(V) oxide, is added in the amount of 3.57% w/w, relative to the starting charge of CL20. Then the mixture is stirred at the temperature of 20° C. for 15 min. After this stirring time period, the solution is filtered, and the filtrate is stirred (400 rpm) and treated with 111 mass parts of chloroform, acting as antisolvent, added dropwise. The final operations are filtration of the obtained suspension and drying of the thus prepared RS-CL20 in a vacuum drying oven for a period of 10 hours. The resulting RS-CL20 has a purity of 99.33% and impact sensitivity of 7.8 J Example 4

Determination of Thermal Stability of CL20 by Means of Differential Thermal Analysis (DTA)

The non-isothermal differential thermal analysis (DTA) working with the linear temperature increase velocity of 5° C./min and sample weights of 50 mg was used to find the peak temperatures of exothermic decomposition of selected samples of CL20 (Table 2).

TABLE 2

Results of DTA measurements

| Sample CL20 | Peak temperature of exothermic decomposition (° C.) |
|---|---|
| α-CL20 | 222.4 |
| batch 26 in Table 1 | 225.4 |
| batch 5 in Table 1 | 224.1 |

The invention claimed is:

1. A method of preparation of ε-2,4,6,8,10,12-hexanitro-2,4,6,8,10,12-hexaazaisowurtzitane with reduced impact sensitivity by precipitation of a solution of 2,4,6,8,10,12-hexanitro-2,4,6,8,10,12-hexaazaisowurtzitane in a solvent by an antisolvent, characterized in that phosphorus(V) oxide is added as a recrystallization promoter to the solution of 2,4,6,8,10,12-hexanitro-2,4,6,8,10,12-hexaazaisowurtzitane in the solvent, the obtained mixture is stirred and filtered, and the filtrate is subsequently precipitated by the addition of the antisolvent.

2. The method according to claim 1, wherein water is removed from the solution before or after the addition of phosphorus(V) oxide.

3. The method according to claim 1, wherein the solvent for the starting 2,4,6,8,10,12-hexanitro-2,4,6,8,10,12-hexaazaisowurtzitane solution is ethyl acetate.

4. The method according to claim 1, wherein the recrystallization promoter phosphorus(V) oxide is added in the amount of 1 to 15% w/w, relative to the weight of 2,4,6,8,10,12-hexanitro-2,4,6,8,10,12-hexaazaisowurtzitane.

5. The method according to claim 1, wherein phosphorus(V) oxide is used together with glycerol as a promoter.

6. The method according to claim 1, wherein the mixture of 2,4,6,8,10,12-hexanitro-2,4,6,8,10,12-hexaazaisowurtzitane solution with the recrystallization promoter is stirred for a time period within the range of 15 to 60 min.

7. The method according to claim 1, wherein the mixture of 2,4,6,8,10,12-hexanitro-2,4,6,8,10,12-hexaazaisowurtzitane solution with the recrystallization promoter is stirred at a temperature within the range of 10 to 40° C.

8. The method according to claim 1, wherein the antisolvent is selected from the group comprising paraffinic hydrocarbons, polychlorinated aliphatic hydrocarbons, and aromatic hydrocarbons.

9. The method according to claim 1, wherein ultrasound is applied during the precipitation step and/or the mixture is stirred.

10. The method according to claim 1, wherein water is removed from 2,4,6,8,10,12-hexanitro-2,4,6,8,10,12-hexaazaisowurtzitane solution in ethyl acetate by means of vacuum azeotropic distillation, subsequently 3.57% w/w, relative to the weight of 2,4,6,8,10,12-hexanitro-2,4,6,8,10,12-hexaazaisowurtzitane, of the recrystallization promoter phosphorus(V) oxide is added to the dehydrated solution, this mixture is stirred for 15 min at the temperature of 20° C., the resulting mixture is filtered and the final product is precipitated by means of addition of n-heptane or xylene as the antisolvent.

* * * * *